United States Patent [19]

Cidaria et al.

[11] Patent Number: 5,126,265
[45] Date of Patent: Jun. 30, 1992

[54] AB-021 ANTIBIOTICS AND PROCESS FOR PRODUCING THEM

[75] Inventors: Dante Cidaria, Novara; Nunzio Andriollo, Bollate; Giorgio Cassani, Arluno; Enrico Crestani, Novara; Silvia Spera, Daverio; Carlo Garavaglia, Cuggiono; Giorgio Pirali, Saronno; Giovanni Confalonieri, Monza, all of Italy

[73] Assignee: Presidenza del Consiglio dei Ministri-Ufficio del Ministro per il coordinamento delle Iniziative per la Ricerca Scientifica e Tecnologica, Rome, Italy

[21] Appl. No.: 441,652

[22] Filed: Nov. 27, 1989

[30] Foreign Application Priority Data

Dec. 1, 1988 [IT] Italy .................. 22808 A/88

[51] Int. Cl.⁵ .............. C07G 11/00; C12P 1/02; C12R 1/465; A61K 35/00
[52] U.S. Cl. .................. 435/253.5; 435/886; 435/171; 424/122; 424/116
[58] Field of Search .......... 435/171, 253.5, 886; 424/122, 116

[56] References Cited

U.S. PATENT DOCUMENTS

| | | |
|---|---|---|
| 3,989,820 | 11/1976 | Florent et al. .......... 424/122 |
| 4,076,802 | 2/1978 | Westley .................. 424/122 |
| 4,132,779 | 1/1979 | Hertz et al. ............ 424/122 |
| 4,133,876 | 1/1979 | Hamill et al. .......... 424/122 |
| 4,705,688 | 11/1982 | Carter et al. .......... 424/122 |
| 4,956,180 | 9/1990 | Cassani et al. ........ 435/169 |

OTHER PUBLICATIONS

Shirling et al., *Int. Journal of Syst. Bact.*, vol. 22(4), 1972, pp. 265-393.

*Primary Examiner*—Ronald W. Griffin
*Assistant Examiner*—Pamela S. Webber
*Attorney, Agent, or Firm*—Stevens, Davis, Miller & Mosher

[57] ABSTRACT

The AB-021 Antibiotics and the main components thereof: AB-021a Antibiotic and AB-021b Antibiotic, obtained by means of the controlled aerobial cultivation of Streptomyces sp. NCIB 40068 in an aqueous nutrient cultivation medium, are disclosed.

The AB-021 Antibiotics show a biological activity against pathogenous fungi of agrarian cultivations, of human pathogenous fungi and of bacteria.

12 Claims, 10 Drawing Sheets

AB-021 ANTIBIOTICS AND PROCESS FOR PRODUCING THEM

The present invention relates to antibiotic substances denominated as "AB-021 Antibiotics" and to the main components thereof: AB-021a Antibiotic and AB-021b Antibiotic.

Furthermore, the present invention relates to the process for preparing said AB-021 Antibiotics by means of the fermentation of Streptomyces sp. NCIB 40068, and to their use in the treatment of the infective diseases caused by microorganisms susceptible to them.

AB-021 Antibiotics, as well as the components thereof, i.e., AB-021a Antibiotic and AB-021b Antibiotic, are different from the other antibiotics known from the prior art.

The term "AB-021 Antibiotics" used in the present invention indicates a mixture which comprises all of the components endowed with biological activity such as, for example, of antifungal and/or antibacterial type, produced by the fermentation of Streptomyces sp. NCIB 40068 under such conditions which will be specified in the following.

Said biologically active components comprise, but are not limited to, those designated as "AB-021a Antibiotic" and "AB-021b Antibiotic", which we were able to isolate from the mixture.

Those skilled in the art of fermentation are well aware of the fact that the number and the mutual ratios of the components which constitute the AB-021 Antibiotics may vary, as a function of the fermentation conditions (such as e.g., the culture medium, fermentation temperature, the duration of the same fermentation, the aeration), and of the bacterial strain used.

One should furthermore understand that the present invention is not limited to the use of Streptomyces sp. NCIB 40068, but comprises also the use of variants and/or mutants as spontaneously or artificially obtained from the above said microorganism, on condition that they produce the AB-021 Antibiotics.

Therefore, the object of the present invention are the AB-021 Antibiotics obtainable by means of the controlled cultivation under aerobial conditions of Streptomyces sp. NCIB 40068, or of an equivalent either spontaneous or artificial variant or mutant thereof, in an aqueous nutrient cultivation medium, containing sources of carbon, nitrogen, inorganic salts and metals in trace amounts, and subsequent separation of said Antibiotics and of the main components thereof: AB-021a and AB-021b Antibiotics.

PHYSICAL-CHEMICAL CHARACTERISTICS OF AB-021a ANTIBIOTIC

Figure 1:
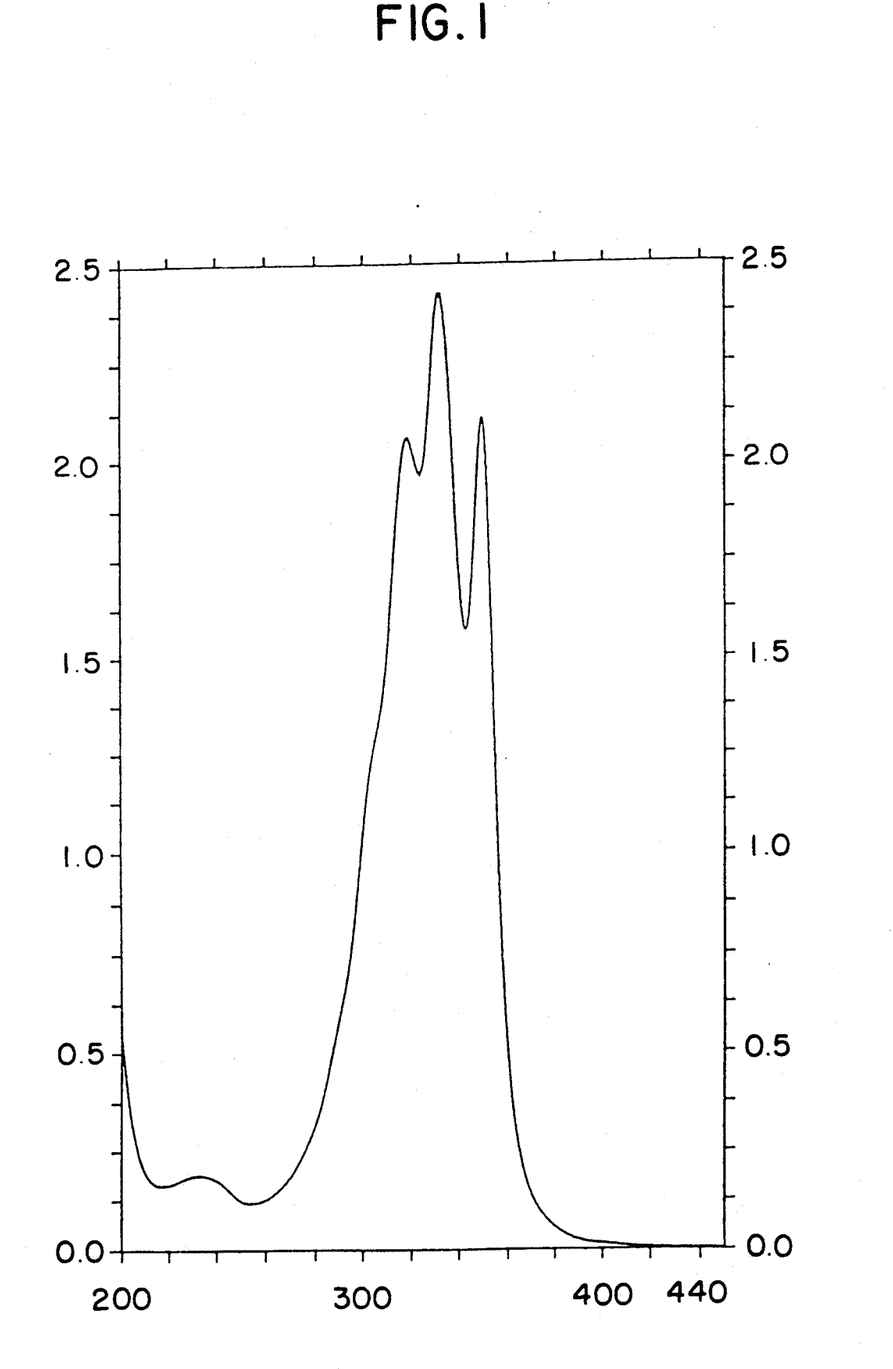
FIG. 1 is a UV absorption spectrum for AB021a antibiotic.
Figure 2:
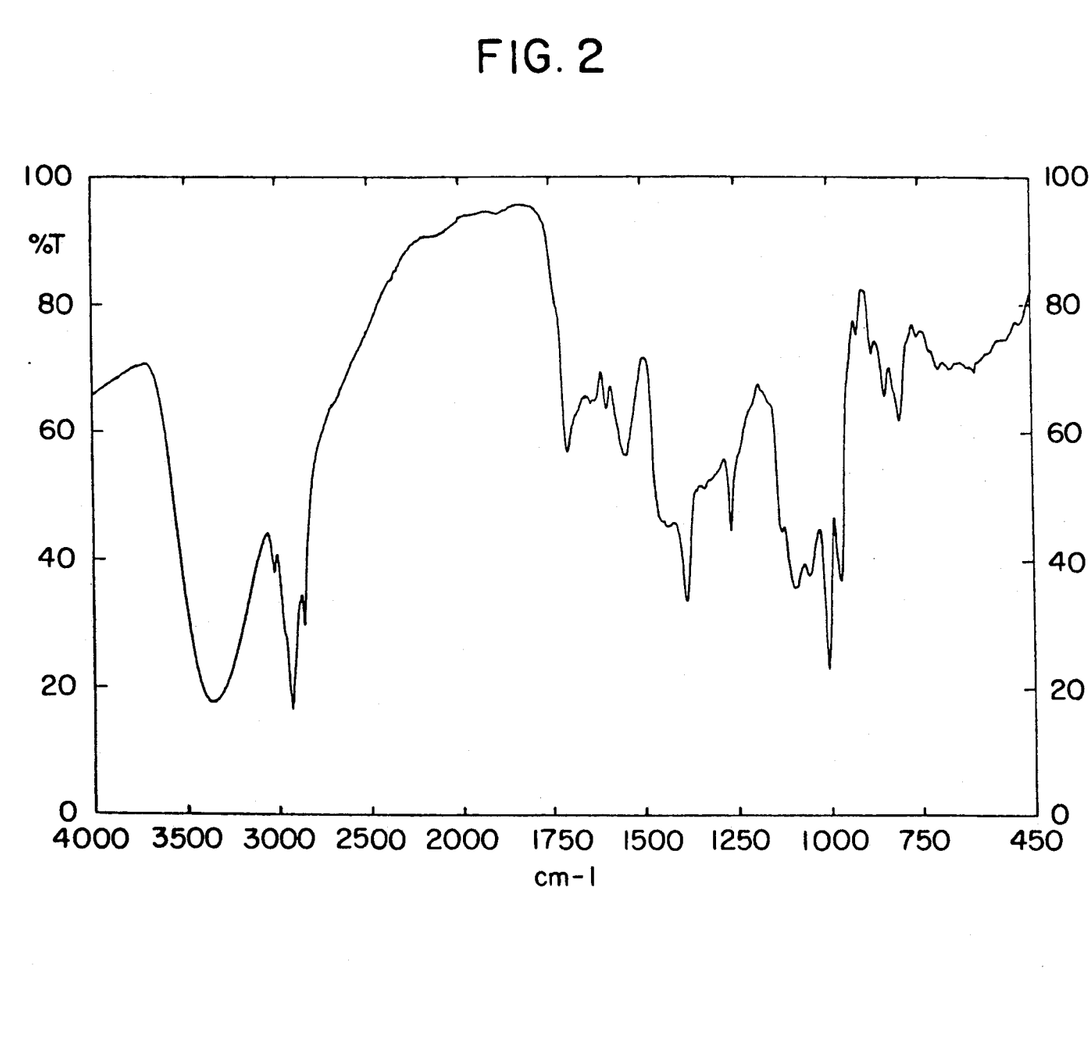
FIG. 2 is an I.R. absorption spectrum in KBr pellet for AB021a antibiotic.
Figure 3:
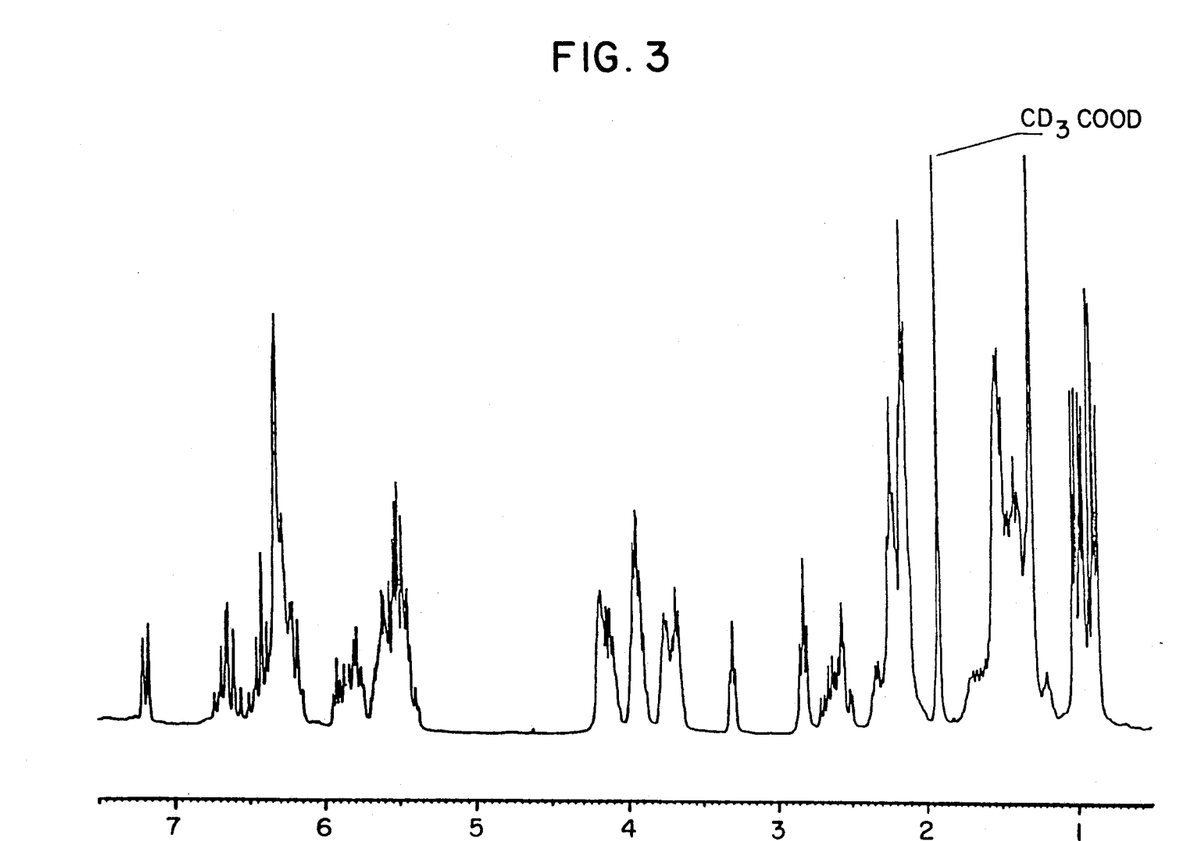
FIG. 3 is a NMR spectrum of $^1H$ for AB021a antibiotic.

AB-021a Antibiotic, a component of AB-021 Antibiotics, is a powder of light yellow colour, characterized by:

(a) a good solubility in dimethylsulfoxide and in (1:1 V/V) ethanol/water or (1:1 V/V) methanol/water blends [V/V=volume/volume], poor solubility in water, rather good solubility in ethanol and methanol;

(b) Approximate elemental analysis, determined on a sample left standing under vacuum at 40° C. for 2 hours, expressed as % values:
carbon: 64.3
hydrogen: 9.15
nitrogen: 1.04;
it contains neither sulfur nor phosphorus;

(c) molecular weight of about 1139, as computed from FAB-MS spectrum, which shows a peak at 1138, corresponding to $(M-H)^-$, under the following operating conditions:
Negative ions, FAB, Xe at 9.5 kV
Matrix: glycerol
Finnigan Mat 8428;

(d) the U.V. absorption spectrum is shown in FIG. 1 of the hereto attached drawings. It shows the absorbance maximum peaks of 0.193 at 232.8 nm; 2.064 at 318.4 nm; 2.44 at 332.6 nm; 2.113 at 349.6 nm; at a concentration of 0.025 mg/ml in 1:1 (V/V) acetonitrile: water;

(e) the infrared (I.R.) absorption spectrum in KBr pellet is reported in FIG. 2 of the hereto attached drawings, and shows the following absorption maxima $(cm^{-1})$: 3365; 3015; 2923; 2851; 1700; 1634; 1594; 1541; 1431; 1380; 1329; 1262; 1128; 1095; 1056; 1004; 968; 919; 878; 843; 804; 754;

(f) the N.M.R. spectrum of $^1H$ is reported in FIG. 3, and shows signals recorded by means of a BRUKER AM 300 MHz spectrometer in hexa-deutero-dimethylsulfoxide (DMSOd6) with the addition of very small amounts of tetradeuterated acetic acid. The chemical shifts were indirectly referred to TMS=0.00 ppm ($\delta$TMS), using as the internal reference the central peak of hexa-deutero-dimethylsulfoxide taken at $\delta$TMS=2.56 ppm:

$\delta$TMS (ppm): 7.18 (d, 1H); 6.69 (dd, 1H); 6.59 (dd, 1H); 6.52–6.09 (m, 9H); 5.96–5.70 (m, 3H); 5.70–5.31 (m, 8H); 4.27–4.02 (m, 4H); 4.02–3.82 (m, 4H); 3.82–3.58 (m, 4H); 3.30 (t, 1H); 2.82 (t, 2H); 2.73–2.45 (\*) (m, 3H); 2.41–1.98 (m, 13H); 1.91 (s, 3H); 1.79–1.12 (m, 24–25H); 1.00 (d, 3H); 0.95 (d, 3H); 0.89 (d, 3H); 0.85 (d, 3H);
(\*) within this range, also the peak of DMSOd6 is comprised.

Figure 4:
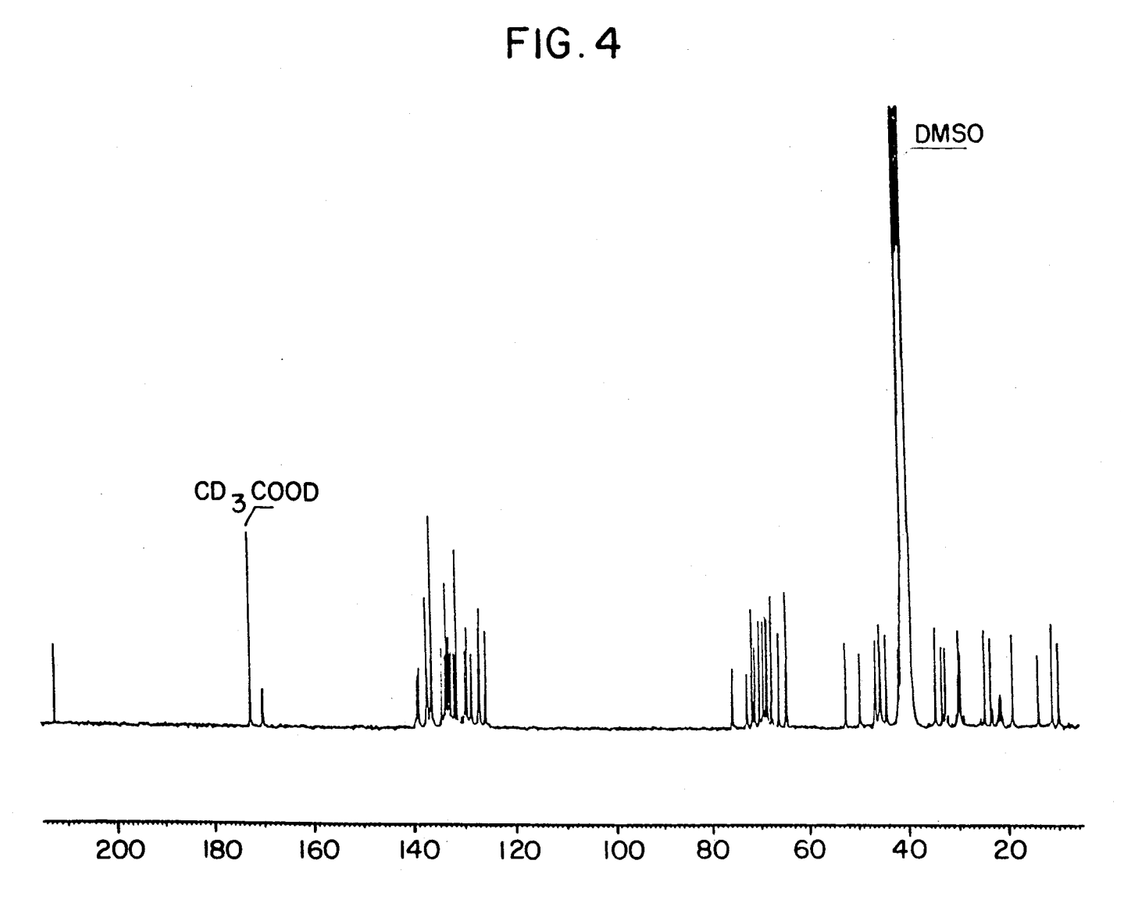
FIG. 4 is a NMR spectrum of $^{13}C$ for AB021a antibiotic.

(g) the N.M.R. spectrum of $^{13}C$ is reported in FIG. 4 and shows signals recorded by means of a BRUKER AM 300 MHz spectrometer in hexa-deutero-dimethylsulfoxide (DMSOd6), with the addition of very small amounts of tetradeuterated acetic acid. The chemical shifts were indirectly referred to TMS=0.00 ppm ($\delta$TMS), using as the internal reference the central peak of hexa-deutero-dimethylsulfoxide taken at $\delta$TMS=39.85 ppm. The data relevant to the multiplicity of the signals were obtained by means of DEPT tests at 45°, 90° and 135°.

δTMS (ppm): 212.1 (s); 169.9 (s); 138.8 (d); 138.5 (d); 137.0 (d); 136.9 (d); 136.7 (d); 136.1 (d); 135.9 (d); 135.9 (d); 134.0 (d); 133.3 (d); 133.0 (d); 132.9 (d); 132.5 (d); 132.4 (d); 132.0 (d); 131.5 (d); 131.0 (d); 131.0 (d); 129.3 (d); 128.9 (d); 128.0 (d); 126.7 (d); 126.4 (d); 125.3 (d); 75.3 (d); 72.3 (d); 71.2 (d); 70.6 (d); 69.7 (d); 68.9 (d); 68.4 (d); 68.0 (d); 67.1 (d); 67.1 (d); 65.7 (d); 64.2 (d); 64.2 (d); 52.1 (d); 41.5 (d); 39.9 (d); 49.2 (t); 46.2 (t); 46.0 (t); 45.2 (t); 45.2 (t); 44.9 (t); 43.9 (t); 41.2 (t); 40.8 (t); 40.7 (t); 39.2 (t); 38.8 (t); 34.1 (t); 32.8 (t); 32.1 (t); 29.3 (t); 24.1 (t); 22.8 (q); 18.4 (q); 13.2 (q); 10.5 (q); 9.1 (q).

(h) the retention coefficients in thin-layer chromatography with a run of the eluent of 15 cm, on Kieselgel 60 F 254 (Merck-Schuchardt) slabs and on reverse-phase silica slabs RP-18 F 254 (Merck-Schuchardt) in the following eluent systems and compared to AB-021b Antibiotic:

A eluent: methanol: acetonitrile: 25 mM monohydrogen sodium phosphate in water (4:4:2);

B eluent: methanol: acetonitrile: 25 mM dihydrogen potassium phosphate − 7 mM tetramethyl-ammonium chloride in water (4:4:2)

C eluent: methanol: 10 mM monohydrogen ammonium phosphate adjusted at pH 7.5 with phosphoric acid, in water (8:2);

D eluent: methanol: acetonitrile: 10 mM monohydrogen ammonium phosphate adjusted at pH 7.5 with phosphoric acid, in water (4:4:2);

E eluent: ethanol: dioxane: aqueous solution of ammonia at 30%: water (8:1:1:1);

F eluent: methylene chloride: methanol (17:3).

| Slab | Eluent | R. (AB-021a) | R. (AB-021b) |
|---|---|---|---|
| RP-18 | A | 0.29 | 0.27 |
| RP-18 | B | 0.39 | 0.35 |
| RP-18 | C | 0.21 | 0.12 |
| RP-18 | D | 0.25 | 0.24 |
| silica | E | 0.47–0.57 | 0.54 |
| silica | F | 0.0 | 0.0 |

Visualization:
A. Fluorescence in U.V. light (366 nm)
B. Anisaldehyde (T-27 reactant)—Thin Layer Chromatography— page 205 Author: Justus G. Kirchner—2nd Ed. Publisher: John Wiley & Sons.
C. o-Aminophenol (T-11 reactant)—Thin Layer Chromatography—page 201 Author: Justus G. Kirchner—2nd Ed. Publisher: John Wiley & Sons.

(i) Retention time ($R_t$) of about 8 minutes when analyzed on reverse-phase HPLC column under the following conditions:
Column: Hibar LichroCART Li-Chrosorb RP-18 (7 microns) 250×4.0 mm (Merck, Darmstadt, F. R. of Germany)
Forecolumn: Guard Pak RCSS C 18 (Millipore Waters)
Eluent: methanol: acetonitrile: 10 mM monohydrogen ammonium phosphate in water (1:1:1)
Flowrate: 0.8 ml/minute
Detector: U.V. at 333 nm
Temperature: 40° C.

Under the same conditions AB-021b Antibiotic is eluted after about 11.8 minutes.

Figure 5:
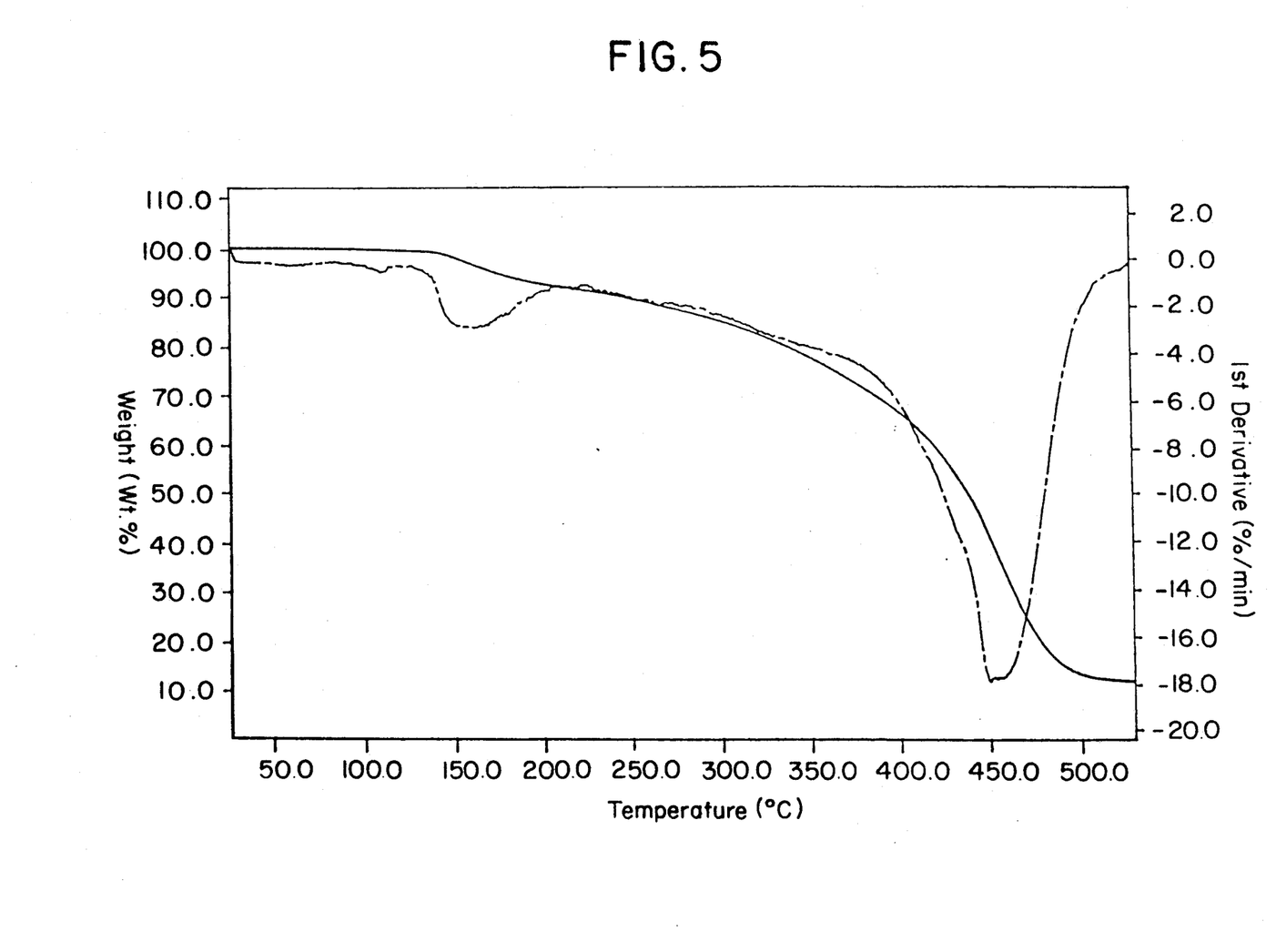
FIG. 5 is a plot of % weight loss vs. temperature in a thermogravimetric analysis of AB021a antibiotic.

(1) The thermogravimetric analysis carried out under nitrogen, with a temperature increase rate of 20° C./minute within the temperature range of from 30° C. up to 700° C. on a PERKIN-ELMER 7 SERIES Thermal Analysis System, shows the trend reported in FIG. 5, in which on the abscissa the temperature is reported as °C., and on the ordinate the percent weight loss is reported. In the same Figure also the first derivative of the curve is reported.

PHYSICAL-CHEMICAL CHARACTERISTICS OF AB-021b ANTIBIOTIC

Figure 6:
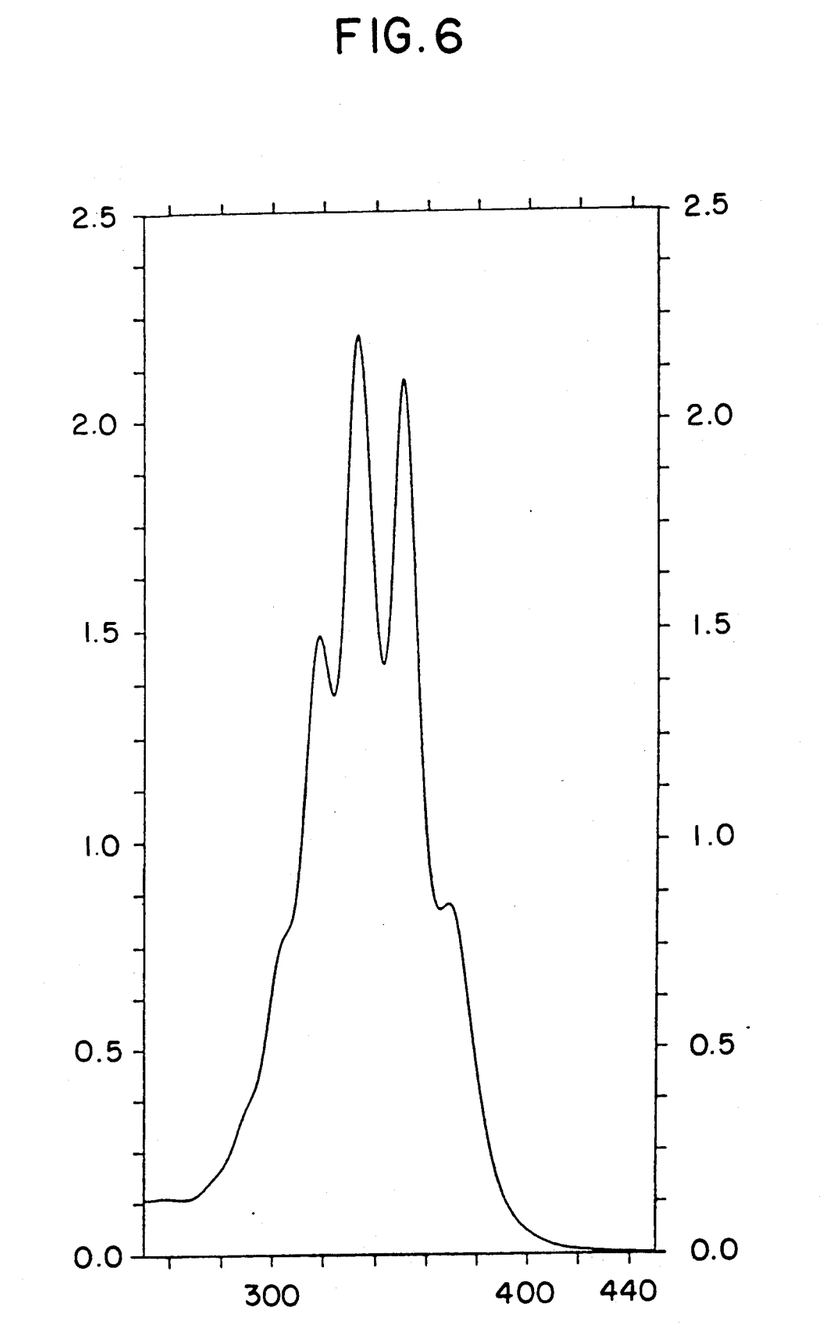
FIG. 6 is a UV absorption spectrum for AB021b antibiotic.
Figure 7:
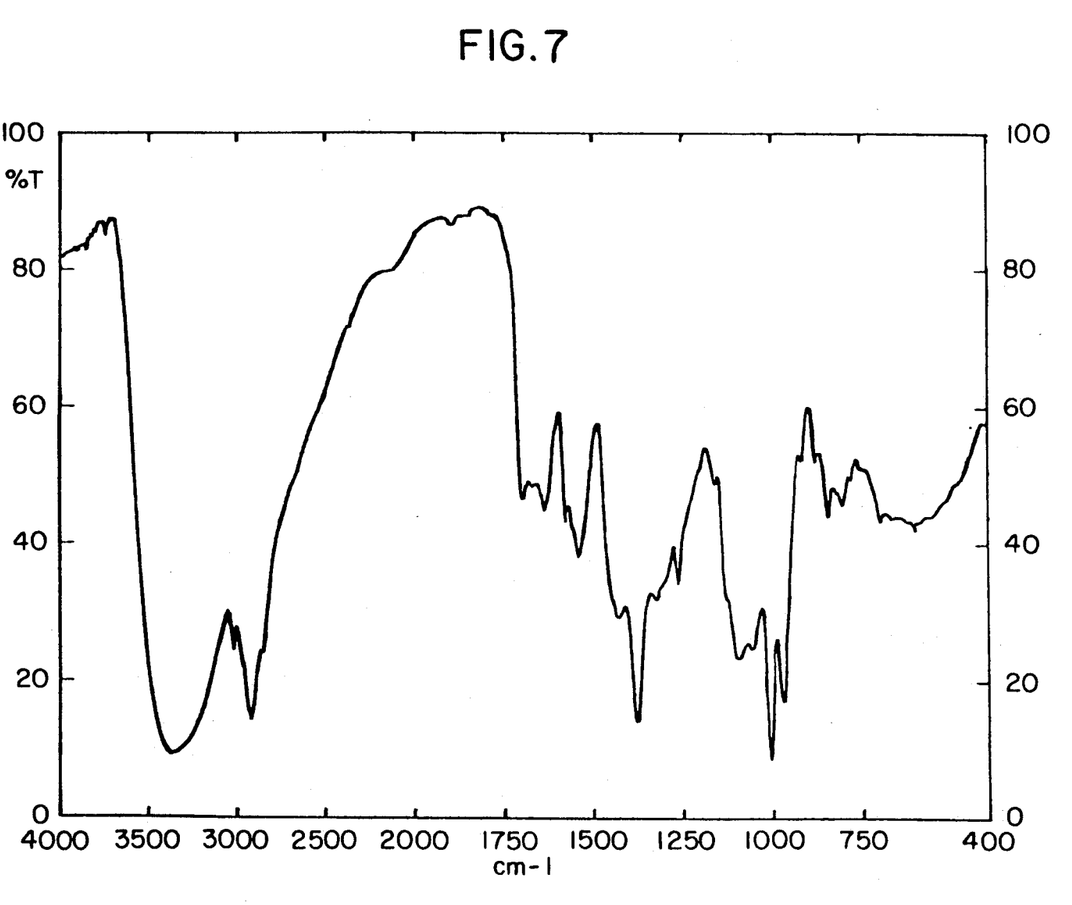
FIG. 7 is an IR absorption spectrum in KBr pellet for AB021b antibiotic.
Figure 8:
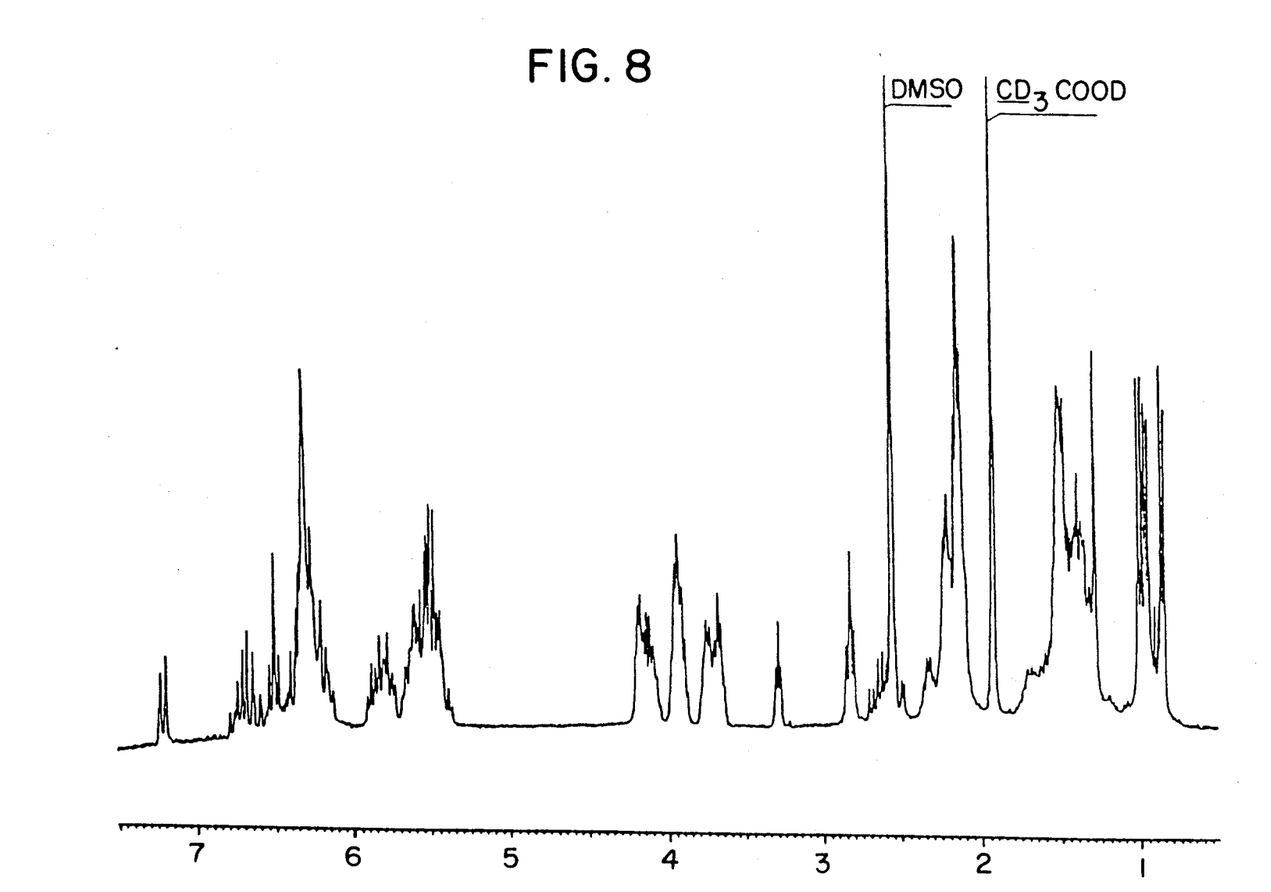
FIG. 8 is a NMR spectrum of $^1H$ for AB021b antibiotic.

AB-021b Antibiotic, a component of AB-021 Antibiotics, is a powder of deep yellow colour, characterized by:

(a) An U.V. absorption spectrum as shown in FIG. 6 of the hereto attached drawings. It shows the following absorbance maxima: 0.90 at 369.0 nm; 2.01 at 350.0 nm; 2.21 at 332.6 nm; 1.49 at 318.0 nm; at a concentration of 0.02 mg/ml in 1:1 (V/V) acetonitrile/water;

(b) Approximate elemental analysis, determined on a sample left standing under vacuum at 40° C. for 2 hours, expressed as % values:
carbon: 65.12
hydrogen: 8.65
nitrogen: 1.18
it contains neither sulfur nor phosphorus;

(c) the infrared (I.R.) absorption spectrum in KBr pellet is reported in FIG. 7 of the hereto attached drawings, and shows the following absorption maxima ($cm^{-1}$): 3902, 3853, 3747, 3375, 3013, 2921, 2853, 2757, 1895, 1699, 1669, 1645, 1576, 1540, 1430, 1378, 1324, 1261, 1160, 1094, 1059, 1004, 969, 919, 878, 843, 803, 779, 697;

d) molecular weight of about 1165 as computed from FAB-MS spectrum, which shows a peak at 1164, corresponding to $(M-H)^-$, under the following operating conditions:
Negative ions, FAB, Xe at 9.5 kV
Matrix: glycerol
Finnigan Mat 8424;

(e) the N.M.R. spectrum of $^1H$ is reported in FIG. 8 of the hereto attached drawings, and shows signals recorded by means of a BRUKER AM 300 MHz spectrometer in hexa-deutero-dimethylsulfoxide (DMSOd6), with the addition of small amounts of tetradeuterated acetic acid. The chemical shifts were indirectly referred to TMS=0.00 ppm (δTMS), using as the internal reference the central peak of hexa-deutero-dimethylsulfoxide taken at δTMS=2.56 ppm:

δTMS (ppm): 7.21 (d, 1H); 6.75 (dd, 1H); 6.63 (dd, 1H); 6.57–6.07 (m, 11H); 5.93–5.70 (m, 3H); 5.70–5.33 (m, 8H); 4.25–4.02 (m, 4H); 4.02–3.83 (m, 4H); 3.83–3.59 (m, 4H); 3.29 (t, 1H); 2.82 (t, 2H); 2.72–2.44 (*) (m, 6–7H); 2.41–2.00 (m, 14H); 1.92 (s, 3H); 1.80–1.14 (m, 21H); 1.00 (d, 3H); 0.95 (d, 3H); 0.84 (d, 3H).
(*) Within this range also the peak of DMSOd6 is comprised.

Figure 9:
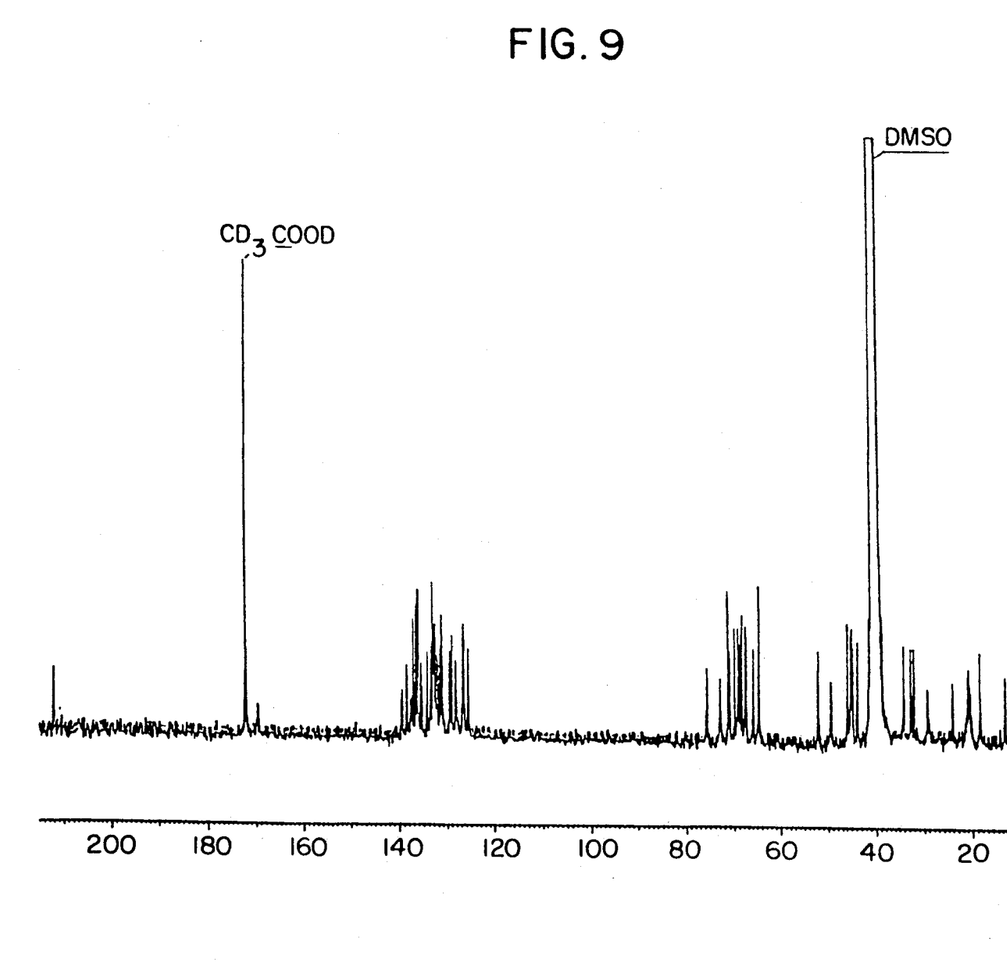
FIG. 9 is the NMR spectrum of $^{13}C$ for AB021b antibiotic.

(f) the N.M.R. spectrum of $^{13}C$ is reported in FIG. 9 of the hereto attached drawings, and shows signals recorded by means of a BRUKER AM 300 MHz spectrometer in hexa-deutero-dimethylsulfoxide (DMSOd6). The chemical shifts were indirectly referred to TMS=0.00 ppm (δTMS), using as the internal reference the central peak of hexa-deutero-dimethylsulfoxide taken at δTMS=39.85 ppm. The data relevant to the multiplicity of the signals were obtained by means of DEPT tests at 45°, 90° and 135°.

δTMS (ppm): 212.0 (s); 169.2 (s); 139.1 (d); 138.1 (d); 137.1 (d); 136.7 (d); 136.2 (d); 135.8 (d); 135.8 (d); 135.1 (d); 133.8 (d); 133.1 (d); 132.8 (d); 132.8 (d); 132.6 (d); 132.3 (d); 132.2 (d); 132.1 (d); 131.8 (d); 131.2 (d); 130.9 (d); 130.8 (d); 129.2 (d); 128.7 (d); 127.9 (d); 126.4 (d);

126.2 (d); 125.2 (d); 75.4 (d); 72.6 (d); 71.0 (d); 70.6 (d); 69.6 (d); 68.9 (d); 68.4 (d); 68.0 (d); 67.3 (d); 67.2 (d); 65.6 (d); 64.4 (d); 64.4 (d); 51.9 (d); 41.3 (d); 39.6 (d); 49.2 (t); 45.8 (t); 45.7 (t); 45.0 (t); 44.9 (t); 44.7 (t); 43.6 (t); 41.1 (t); 40.7 (t); 40.5 (t); 39.0 (t); 38.7 (t); 33.9 (t); 32.5 (t); 31.9 (t); 29.0 (t); 23.9 (t); 18.1 (q); 12.8 (q); 10.4 (q); 8.7 (q).

Figure 10:
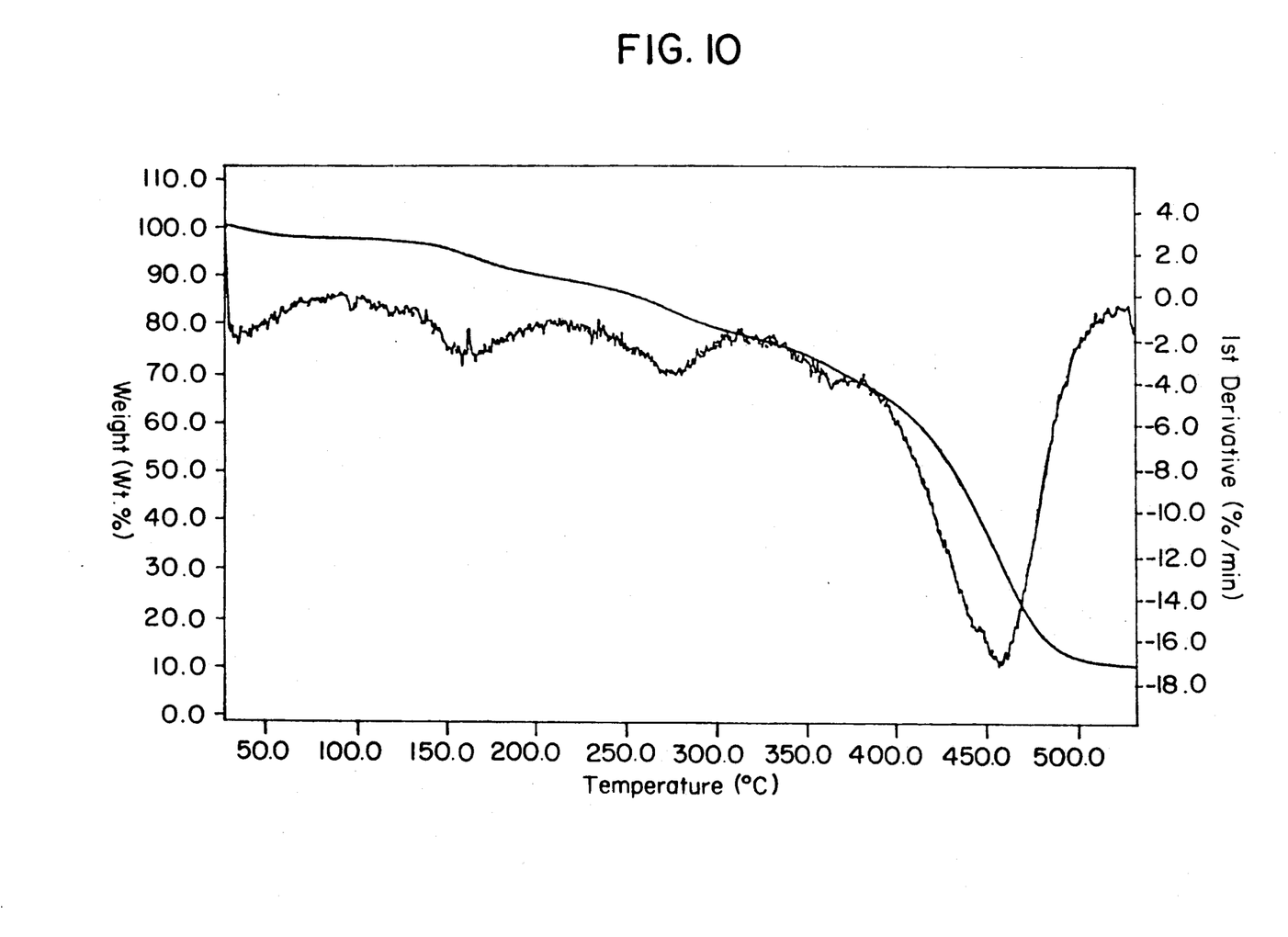
FIG. 10 is a plot of % weight loss vs. temperature in a thermogravimetric analysis of AB021b antibiotic.

(g) The thermogravimetric analysis carried out under nitrogen, with a temperature increase rate of 20° C./minute within the temperature range of from 30° C. up to 700° C. on a PERKIN-ELMER 7 SERIES Thermal Analysis System, shows the trend reported in FIG. 10, in which on the abscissa the temperature is reported as °C., and on the ordinate the percent weight loss is reported. In the same Figure also the first derivative of the curve is reported.

(h) the retention coefficients ($R_f$) in thin-layer chromatography and the retention times ($R_t$) on reverse-phase HPLC column are respectively reported under (h) and (i) paragraphs of the description of the physical-chemical characteristics of AB-021a Antibiotic.

Morphology and Cultural Characteristics of Microorganism Streptomyces sp. NCIB 40068

The microorganism Streptomyces sp. NCIB 40068 was isolated from a sample of soil collected at Cappella di Terza (Novara), and catalogued for internal laboratory use under the conventional name of SD-505ω.

A culture of this microorganism was filed on Sep. 29th 1988, in compliance with the Treaty of Budapest, with the National Collection of Industrial Bacteria (c/o the National Collection of Industrial and Marine Bacteria Ltd., Torry Research Station, P.O. Box 31, 135 Abbey Road, Aberdeen AB 98 DG, Scotland, United Kingdom), where it was given the access name of NCIB 40068.

The morphologic characteristics of the strain are reported in Table A (the names of the culture media are those as reported by the International Streptomyces Program).

TABLE A

| ISP Code | Culture Medium | Description |
|---|---|---|
| — | Nutrient Agar | Plentiful growth, light-yellow coloured, not spored mycelium. |
| M3 | Oat Meal | Scarce growth, light-yellow coloured, not spored mycelium. |
| — | Czapek Dox | Plentiful growth, light-yellow coloured, not spored mycelium. |
| M4 | Starch Agar | Plentiful growth, light-yellow coloured, not spored mycelium. |
| M5 | Glycerol Asparagine Agar | Plentiful growth, light-yellow coloured, not spored mycelium. |
| M6 | Peptone Iron Agar | Plentiful growth, light-yellow coloured, not spored mycelium |

In Tables B and C, some characteristics of this strain are reported.

TABLE B

| Characteristic | Response |
|---|---|
| Growth at 4° C. | negative |
| Growth at 45° C. | poor |
| Resistance to Lysozyme | 10 ppm |
| Resistance to Rifampicin | 2 ppm |
| Resistance to Oxytetracycline | 8 ppm |

TABLE C

| Growth on one single carbon source | |
|---|---|
| Carbon source | Growth |
| 2-keto-gluconate | rather good |
| adonitol | rather good |
| arabinose | good |
| cellobiose | none |
| galactose | good |
| glycerol | rather good |
| inositol | none |
| lactose | none |
| maltose | good |
| melezitose | rather good |
| methyl-D-glucoside | rather good |
| N-acetyl-D-glucosamine | good |
| raffinose | none |
| saccharose | rather good |
| sorbitol | none |
| trehalose | good |
| xylitol | good |
| xylose | rather good |

The analysis of the cellular wall of Streptomyces sp. NCIB 40068 was carried out according to the method described by M. P. Starr, H. Stolp, H. G. Truper, A. Ballows, H. G. Shegel in "The Prokaryotes"- Vol. II Streptomycetacee—Springer Verlag Ed., 1981). Such an analysis demonstrates the absence of characteristic sugars; it confirms hence the belonging of SD-505W strain to Streptomyces genus.

Like other microorganisms, Streptomyces sp. NCIB 40068 can undergo variations and/or mutations of either spontaneous or artificial character.

For example, artificial variants or mutants can be obtained by treating the microorganism with chemical mutagen agents, such as, e.g., nitrous acid, nitrosoguanidine, halogenated alkylamines and the like, or with physical agents, such as X rays or U.V. light, high-frequency waves.

Spontaneous variants or mutants can be obtained as well by isolating and selecting different colonies obtained from Streptomyces sp. NCIB 40068.

All of the variants and/or mutants, both of natural origin, or man-made, which belong to Streptomyces species and produce AB-021 Antibiotics are regarded as equivalent to Streptomyces sp. NCIB 40068 microorganism and are included within the purview of the present invention.

Process of Preparation of AB-021 Antibiotics

The process for the preparation of AB-021 Antibiotics consists in cultivating Streptomyces sp. NCIB 40068, or an equivalent either spontaneous or man-made variant or mutant thereof, under conditions of controlled aerobial fermentation in an aqueous nutrient medium, and in subsequently separating said AB-021 Antibiotic by means of per se known methods.

The nutrient culture media or fermentation broths can be used, which are customarily used for the production of antibiotics; however, some nutrient culture media result to be preferred.

Said cultivation media should contain sources of carbon and nitrogen assimilable by the microorganisms of Streptomyces genus, and, furthermore, low levels of inorganic salts.

They should furthermore contain traces of the metals necessary for the growth and the development of the microorganisms, and for the production of the antibiotics. Said metal traces can be already present as impurities in the sources of carbon and of organic nitrogen supplied in the culture media for the bacterial growth, or, whenever necessary, they can be added to the same culture media.

As a carbon source, carbohydrates can be generally used, in particular saccharides, such as, e.g., dextrose or maltose, or, as an alternative, or as a complement, starches, and products which can be assimilated to starches from an industrial standpoint, such as, e.g., dextrin or soluble starch, or also polyalcohols, such as, e.g., glycerol.

Said compounds can be used either individually, or combined with one another in variable proportions.

The concentration and type of the source of carbon in the culture medium generally depend on the type and amount of the other ingredients contained in said medium; anyway, concentrations comprised within the range of from 0.5 to 5% by weight are generally satisfactory.

As the source of organic nitrogen, both proteinic extracts such as, e.g., yeast extract, meat extract or casein hydrolisate, or meals, such as, e.g., soybean meal, or industrial products available on the market for that purpose, such as, e.g., Proflo, Corn Steep Liquor or Distillers' Solubles, can be used.

These compounds can be used both individually and combined with one another, in variable proportions. The concentrations in the culture medium can be comprised within the range of from 0.2% to 6% by weight.

As the inorganic salts, there can be used, for example, sodium salts, potassium salts, magnesium salts, ammonium salts, calcium salts, such as phosphates, sulfates, chlorides, carbonates and nitrates.

The trace metals contained in the culture medium can be, e.g., cobalt, iron, manganese, and the like.

Some culture media displayed a particular ability to stimulate the production of AB-021 Antibiotics by Streptomyces sp. NCIB 40068; among these, for example, the following aqueous formulations can be mentioned, which are used in the preparation Examples set forth in the following.

| Ingredients | Concentration g/l |
|---|---|
| "A" (PMS) CULTURE MEDIUM | |
| Starch | 20 |
| Glucose | 10 |
| Calcium carbonate | 3 |
| Casein hydrolysate | 2 |
| Proflo | 2 |
| Yeast extract | 2 |
| Meat extract | 2 |
| pH | 7.0 |
| "B" (PGC) CULTURE MEDIUM | |
| Glycerol | 30 |
| Proflo | 20 |
| CaCO$_3$ | 3 |
| pH | 6.5-7.0 |
| "C" (SCM) CULTURE MEDIUM | |
| Starch | 10 |
| Glucose | 5 |
| Hydrolysed casein | 1 |
| KNO$_3$ | 2 |
| NaCl | 2 |
| K$_2$HPO$_4$ | 2 |
| MgSO$_4$.7H$_2$O | 0.5 |
| CaCO$_3$ | 1 |
| Fe$_2$SO$_4$.7H$_2$O | 0.01 |
| pH | 7.1 |

The strain of Streptomyces sp. NCIB 40068 can be cultivated and fermented at temperatures comprised within the range of from 20° C. to 35° C., preferably of from 25° C. to 30° C.

The pH value can generally be comprised within the range of from about 5 to about 9.

The sterile air which is injected into the culture medium is generally used in such amounts as to maintain in the medium an oxygen concentration higher than 20% of saturation value.

The production of AB-021 Antibiotics, during the fermentation, can be monitored by means of tests of antibiotic activity on broth samples, using microbial and fungal species sensitive to the same Antibiotics, or by HPLC analysis.

The fermentation is carried out for such a time as to obtain a substantial antibiotic activity; times of from 24 to 150 hours are generally sufficient.

Separation and Purification of the Antibiotics

After the cultivation under the above disclosed fermentation conditions, AB-021 Antibiotics and the main components thereof: AB-021a Antibiotic and AB-021b Antibiotic can be separated from the culture broth and subsequently purified by means of conventional methods of the art of fermentations.

Such methods include, e.g., the extraction with solvents, the precipitation with non-solvents, ultrafiltration, column chromatography, silica-gel chromatography, cellulose chromatography, reverse-phase chromatography, chromatography on non-ionic, macroporous resins, and the like.

The antibiotics produced during the fermentation can be found in the culture broth and/or in the mycelium mass.

A preferred method for recovering AB-021 Antibiotics consists in filtering off the mycelium mass from the culture broth, submitting the so-separated mycelium to an extraction with acetone or methanol, concentrating the extract under vacuum until the complete disappearance of the solvent, with an aqueous suspension being obtained.

The so obtained culture broth containing AB-021 Antibiotics is filtered through fiberglass filters and is then percolated on a column of a non-ionic polystyrene resin, such as, e.g., XAD-2 resin (Rohm & Haas Co.), which adsorbs AB-021 Antibiotics.

The resin is then washed with two volumes, referred to its bed, of water, and is then eluted with three volumes, still referred to its bed, of an 8:2 (V/V) mixture of acetone:water.

The fractions which contain AB-021 Antibiotics, identified by means of biological tests of activity on Botrytis, are combined with one another and are then concentrated under vacuum until the disappearance of solvent, and the so obtained aqueous suspension is combined with the one previously obtained from mycelium in order to yield a raw product containing AB-021 Antibiotics.

The two pure components AB-021a Antibiotic and pure AB-021b Antibiotic are then isolated from the raw product by means of chromatography on reverse phase, using a column packed with silica of MATREX silica C18 type (by Amicon Europe, Lausanne, Switzerland), with an eluent system formed by an "A" eluent consisting of water containing 10 mM monohydrogen ammonium phosphate and by a "B" eluent consisting of methanol, using a linear gradient of from 30% up to 70% of "B" eluent in "A" eluent.

The fractions which contain AB-021a Antibiotic in a pure state and AB-021b Antibiotic in a pure state are separately concentrated under vacuum until complete disappearance of methanol and, by cooling down to 2° C. the remaining aqueous solutions, the precipitation is respectively obtained of AB-021a Antibiotic and AB-021b Antibiotic, which are centrifuged off. AB-021a Antibiotic and AB-021b Antibiotic, so separated from their respective solutions are suspended in water and centrifuged again and, after removing the supernatant solutions, and drying under vacuum at 40° C. for 2 hours, pure AB-021a Antibiotic and pure AB-021b antibiotic are respectively obtained.

BIOLOGICAL ACTIVITY

AB-021 Antibiotics, and the components thereof, i.e., AB-021a Antibiotic and AB-021b Antibiotic, are endowed with antifungal and antibacterial activity.

Their antifungal activity results to be particularly high against phytopathogenous fungi which infest agrarian cultivations of cereals, fruit trees and horticultural cultivations, as well as against pathogen fungi in man.

The antifungal activities, both in vitro and in vivo, of AB-021 Antibiotics were determined by means of the hereinunder described methods.

TEST FOR "IN VITRO" ANTIFUNGAL AND BACTERIDICE ACTIVITY

The antimicrobial activity of AB-021 antibiotics is determined by means of the usual methods, by adding increasing concentrations of the Antibiotic, to an agarized culture medium capable of supporting the growth of the sensitive microbial species.

For phytopathogenous fungi, the minimum concentration of AB-021 Antibiotics was furthermore determined which, under these conditions causes, a reduction in mycelial growth of at least 50% as referred to the control ($ED_{50}$). For yeast (*Candida albicans*) and bacterium (*Sarcina lutea*), the minimum concentration was determined, which completely inhibith growth (MIC).

In D and E Tables, the data of biological activity are reported, which were obtained in vitro by means of the just described methods.

TABLE D

| TEST FUNGUS | AB-021a ($ED_{50}$, ppm) | AB-021b ($ED_{50}$, ppm) |
|---|---|---|
| Botrytis cinerea | 0.065 | 0.088 |
| Helminthosporium teres | 0.024 | <0.01 |
| Helminthosporium gramineum | 0.065 | 0.17 |
| Helminthosporium sativum | 0.15 | 0.22 |
| Fusarium roseum | 0.068 | 0.22 |
| Rhizoctonia solani | 0.093 | 0.15 |
| Colletotrichum coffeanum | 0.012 | 0.015 |
| Piricularia oryzae | 0.6 | 2.5 |
| Septoria nodorum | 1 | 0.16 |
| Guignardia bidwellii | 0.13 | 0.17 |

TABLE E

| MICROORGANISM | AB-021a (MIC, ppm) | AB-021b (MIC, ppm) |
|---|---|---|
| Sarcina lutea | 4 | 2 |
| Candida albicans | 0.6 | 0.1 |

FUNGICIDAL ACTIVITY "IN VIVO"

The fungicidal activity in vivo is measured by using the following method. AB-021 Antibiotics in water-acetone solution at 20% of acetone V/V are sprinkled onto the lower blades of leaves of plants grown in pot inside a conditioned room.

One day later, an inoculum of the tested fungus is sprayed on the upper blade of the leaves of said plants, and these latter are kept under incubation conditions inside a conditioned room for about eight days.

At the end of said time, the seriousness of the infection is evaluated by means of scores of an evaluation scale ranging from 100 (=healthy plant) down to 0 (=completely infected plant).

The data relevant to the preventive activity in vivo as obtained by means of the just described method is reported in Table E.

TABLE E

| Fungus | AB-021 Antibiotics concentration, g/l | Preventive activity |
|---|---|---|
| Plasmopara viticola | 0.5 | 97 |
|  | 0.25 | 80 |
| Sphaeroteca fuliginea | 0.5 | 80 |
|  | 0.25 | 50 |
| Botrytis cinerea | 0.5 | 90 |
|  | 0.25 | 70 |

Strictly analogous results of antifungal activity are obtained by using the individual antibiotics: AB-021a Antibiotic and AB-021b Antibiotic.

For the purposes of their practical use, both in agriculture and in other sectors of use, the antibiotics according to the present invention should be suitably used as suitable formulations.

These formulations contain, besides the antibiotic according to the present invention as their active principle, inert solid carriers (e.g., kaolin, silica, talc, attapulgite, diatomaceous earth, and so forth), or inert liquid carriers (e.g., organic solvents, vegetable or mineral oils, water and their mixtures), and possibly other additives which are normally used in the art of formulations, such as surfactants, suspending agents, dispersants and wetting agents.

In case of particular applicative requirements, or in order to expand the range of action of the formulations, to the above said compositions, other active ingredients, such as e.g., other insecticides, herbicides and fungicides can be added.

The applicative doses vary as a function of different factors, such as the type and the degree of infestation, the type of composition used, climatic and environmental factors.

For practical uses in agriculture, doses of AB-021 Antibiotics comprised within the range of from 10 to 500 g/ha yield satisfactory results.

The following examples are supplied for the purpose of illustrating the invention without limiting it.

EXAMPLE 1

A culture of Streptomyces sp. NCIB 40068 grown on a slant of hereinabove described "A" (PM8) medium, thickened with agar, is suspended back in 5 ml of sterile distilled water. Such a suspension is used in order to inoculate an Erlenmeyer flask containing 100 ml of "A" (PM8) medium, which is subsequently kept stirred at 180 rpm, at 28° C. for 55 hours. Such a culture is used in order to inoculate an Erlenmeyer flask containing 1000 ml of "A" (PM8) medium, which is subsequently kept stirred at 150 rpm, and 28° C. for 40 hours. With such a culture a fermenter of 40 liters of rated capacity, containing 28 liters of "B" (PGC) medium is then inoculated.

With temperature being kept controlled at 28° C. and with the concentration of dissolved oxygen being kept higher than 20% of saturation value, the fermentation is carried out for 74 hours.

SEPARATION OF AB-021 ANTIBIOTICS 28 liters of fermentation broth obtained as disclosed hereinabove is centrifuged and the so separated mycelium is extracted with 7 liters of acetone.

The acetonic extract is concentrated under vacuum until the total disappearance of the solvent and the residual aqueous solution containing AB-021 Antibiotics (about 1 liter) is collected with 400 ml of methanol, and is chromatographed on a column (inner diameter of 90 mm × 360 mm of length) containing 1.0 kg of silica of MATREX Silica C18 type (Amicon Europe, Lausanne, Switzerland), with a forecolumn (50 mm × 50 mm) packed with the same stationary phase, with an eluent system being used, which is formed by an "A" eluent constituted by water containing 10 mM monohydrogen ammonium phosphate and a "B" eluent constituted by methanol, and with a gradient according to the following Table being used:

| A/B (V/V) | Volume (ml) |
|---|---|
| 70/30 | 750 |
| 65/35 | 750 |
| 60/40 | 750 |
| 55/45 | 750 |
| 50/50 | 750 |
| 45/55 | 750 |
| 40/60 | 750 |
| 35/65 | 750 |
| 30/70 | 20000 |

Pure AB-021a Antibiotic is collected in 2550 ml within the elution range comprised between 15000 and 17550 ml, whilst AB-021b Antibiotic is collected in 3000 ml within the elution range comprised between 21450 and 24450 ml.

The so collected fractions are evaporated under vacuum until methanol is totally disappeared, and are then left standing for 24 hours at 4° C. From these solutions, AB-021a Antibiotic and AB-021b Antibiotic respectively precipitate, and are collected by centrifugation. The centrifuge cakes are then suspended again in water in order to remove any residual salt traces, and are centrifuged again.

After drying, 198 mg of AB-021a Antibiotic, a light-yellow coloured powder, and 210 mg of AB-021b Antibiotic, a yellow-coloured powder, are obtained.

The physical-chemical characteristics of the products have been reported hereinabove.

EXAMPLE 2

A culture of Streptomyces sp. NCIB 40068 grown on a slant of agarized "A" (PM8) medium is suspended again in 6 ml of sterile distilled water. Such a suspension is used in order to inoculate 3 Erlenmeyer flasks, each containing 100 ml of "A" (PM8) medium. The inoculated Erlenmeyer flasks are then kept stirred at 180 rpm, at 28° C. for 48 hours. The so obtained culture is used in order to inoculate 50 Erlenmeyer flasks each containing 100 ml of "B" (PGC) medium, with an inoculum of 5% of the volume. The Erlenmeyer flasks are kept stirred at 180 rpm, at 28° C. for 72 hours. The so-obtained broth is then collected and separated from mycelium by means of centrifugation at 6000 rpm for 20 minutes.

EXAMPLE 3

A culture of Streptomyces sp. NCIB 40068 grown on a slant of agarized "A" (PM8) medium is suspended again in 5 ml of sterile distilled water. Such a suspension is used in order to inoculate an Erlenmeyer flask containing 100 ml of "A" (PM8) medium. The inoculated Erlenmeyer flask is then kept stirred at 180 rpm, at 28° C. for 48 hours.

The so obtained culture is used in order to inoculate 3 Erlenmeyer flasks each containing 100 ml of "C" (SCM) medium, with an inoculum of 5% of the volume. The Erlenmeyer flasks are kept stirred at 180 rpm, at 30° C. for 24–72 hours. At the end of fermentation, the so-obtained broth is separated from mycelium by means of centrifugation, which is carried out in the same way as shown in Example 2.

We claim:

1. AB-021a Antibiotic, which is a solid substance wherein the antibiotic possesses the following characteristics and properties:

(a) a good solubility in dimethylsulfoxide and in (1:1 V/V) ethanol/water or (1:1 V/V) methanol/water blends wherein V/V = volume/volume, poor solubility in water, and rather good solubility in ethanol and methanol;

(b) an approximate elemental analysis, expressed as % values of:
   carbon: 64.3
   hydrogen: 9.15
   nitrogen: 1.04

(c) a molecular weight of about 1139;

(d) maximum absorbance peaks in U.V. light of: 0.193 at 232.8 nm; 2.064 at 318.4 nm; 2.44 at 332.6 nm; 2.113 at 349.6 nm, at a concentration of 0.025 mg/ml of 1:1 (V/V) acetonitrile/water.

(e) maximum absorbance peaks in infrared light at (cm$^{-1}$): 3365; 3015; 2923; 2851; 1700; 1634; 1594; 1541; 1431; 1380; 1329; 1262; 1128; 1095; 1056; 1004; 968; 919; 878; 843; 804; 754;

(f) $^1$H-N.M.R. spectrum, main peaks:
   $\delta$TMS (ppm): 7.18 (d, 1H); 6.69 (dd, 1H); 6.59 (dd, 1H); 6.52–6.09 (m, 9H); 5.96–5.70 (m, 3H); 5.70–5.31 (m, 8H); 4.27–4.02 (m, 4H); 4.02–3.82 (m, 4H); 3.82–3.58 (m, 4H); 3.30 (t, 1H); 2.82 (t, 2H); 2.73–2.45 (*) (m, 3H); 2.41–1.98 (m, 13H); 1.91 (s, 3H); 1.79–1.12 (m, 24–25H); 1.00 (d, 3H); 0.95 (d, 3H); 0.89 (d, 3H); 0.85 (d, 3H);
   (*) within this range, the peak of DMSOd$^6$ is found;

(g) $^{13}$C-N.M.R. spectrum, main peaks:
   $\delta$TMS (ppm): 212.1 (s); 169.9 (s); 138.8 (d); 138.5 (d); 137.0 (d); 136.9 (d); 136.7 (d); 136.1 (d); 135.9 (d); 135.9 (d); 134.0 (d); 133.3 (d); 133.0 (d); 132.9 (d); 132.5 (d); 132.4 (d); 132.0 (d); 131.5 (d); 131.0 (d); 131.0 (d); 129.3 (d); 128.9 (d); 128.0 (d); 126.7 (d); 126.4 (d); 125.3 (d); 75.3 (d); 72.3 (d); 71.2 (d); 70.6 (d); 69.7 (d); 68.9 (d); 68.4 (d); 68.0 (d); 67.1 (d); 67.1 (d); 65.7 (d); 64.2 (d); 64.2 (d); 52.1 (d); 41.5 (d); 39.9 (d); 49.2 (t); 46.2 (t); 46.0 (t); 45.2 (t); 45.2 (t); 44.9 (t); 43.9 (t); 41.2 (t); 40.8 (t); 40.7 (t); 39.2 (t); 38.8 (t); 34.1 (t); 32.8 (t); 32.1 (t); 29.3 (t); 24.1 (t); 22.8 (q); 18.4 (q); 13.2 (q); 10.5 (q); 9.1 (q);

(h) $R_f$ values by thin-layer chromatography (TLC) on 60F 254 slab (Merck-Schuchardt):
0.47-0.57 in ethanol:dioxane:aqueous solution of ammonia at 30%:water (8:1:1:1);
0.0 in 17:3 methylene chloride:methanol
$R_f$ values by reverse-phase chromatography on Merck-Schuchardt RP-18F 254 slab:
0.29 in methanol:acetronitrile:25 mM monohydrogen sodium phosphate in water (4:4:2);
0.39 in methanol:acetronitrile:25 mM dihydrogen potassium phosphate+7 mM tetramethylammonium chloride in water (4:4:2);
0.21 in methanol:10 mM solution of monohydrogen ammonium phosphate adjusted at pH 7.5 with phosphoric acid, in water (8:2);
0.25 in methanol:acetonitrile:10 mM solution of monohydrogen ammonium phosphate adjusted at pH 7.5 with phosphoric acid, in water (4:4:2); and
(i) a retention time ($R_t$) of 8 minutes by reverse-phase HPLC on Hibar Li-ChroCART Li-Chrosorb RP-18 column, forecolumn:Guard Pak RCSS C 18, eluting with methanol:acetronitrile:10 mM aqueous solution of monohydrogen ammonium phosphate (1:1:1), with a flowrate of 0.8 mL/minute at 40° C.

2. AB-021b Antibiotic, which is a solid substance wherein the Antibiotic possesses the following characteristics and properties:
   (a) maximum absorbance peaks in U.V. light of: 0.90 at 369.0 nm; 2.01 at 350 nm; 2.21 at 332.6 nm; 1.49 at 318.0 nm at a concentration of 0.02 mg/ml in 1:1 (V/V) acetronitrile/water;
   (b) maximum absorbance peaks in infrared light at (cm$^{-1}$): 3902, 3853, 3747, 3375, 3013, 2921, 2853, 2757, 1895, 1699, 1669, 1645, 1576, 1540, 1430, 1378, 1324, 1261, 1160, 1094, 1059, 1004, 969, 919, 878, 843, 803, 779, 697;
   (c) molecular weight of about 1165;
   (d) $^1$H-N.M.R. spectrum, main peaks:
   $\delta$TMS (ppm): 7.21 (d, 1H); 6.75 (dd, 1H); 6.63 (dd, 1H); 6.57-6.07 (m, 11H); 5.93-5.70 (m, 3H); 5.70-5.33 (m, 8H); 4.25-4.20 (m, 4H); 4.02-3.83 (m, 4H); 3.83-3.59 (m, 4H); 3.29 (t, 1H); 2.82 (t, 2H); 2.72-2.44 (*) (m, 6-7H); 2.41-2.00 (m, 14H); 1.92 (s, 3H); 1.80-1.14 (m, 21H); 1.00 (d, 3H); 0.95 (d, 3H); 0.84 (d, 3H);
   (*) within this range is found the peak of DMSOd$^6$.
   (e) $^{13}$C-N.M.R. spectrum, main peaks:
   $\delta$TMS (ppm): 212.0 (s); 169.2 (s); 139.1 (d); 138.1 (d); 137.1 (d); 136.7 (d); 136.2 (d); 135.8 (d); 135.8 (d); 135.1 (d); 133.8 (d); 133.1 (d); 132.8 (d); 132.8 (d); 132.6 (d); 132.3 (d); 132.2 (d); 132.1 (d); 131.8 (d); 131.2 (d); 130.9 (d); 130.8 (d); 129.2 (d); 128.7 (d); 127.9 (d); 126.4 (d); 126.2 (d); 125.2 (d); 75.4 (d); 72.6 (d); 71.0 (d); 70.6 (d); 69.6 (d); 68.9 (d); 68.4 (d); 68.0 (d); 67.3 (d); 67.2 (d); 65.6 (d); 64.4 (d); 64.4 (d); 51.9 (d); 41.3 (d); 39.6 (d); 49.2 (t); 45.8 (t); 45.7 (t); 45.0 (t); 44.9 (t); 44.7 (t); 43.6 (t); 41.1 (t); 40.7 (t); 40.5 (t); 39.0 (t); 38.7 (t); 33.9 (t); 32.5 (t); 31.9 (t); 29.0 (t); 23.9 (t); 18.1 (q); 12.8 (q); 8.7 (q);
   (f) $R_f$ values by thin-layer chromatography (TLC) on 60F 254 slab (Merck-Schuchardt):
   0.54 in ethanol:dioxane:aqueous solution of ammonia at 30%:water (8:1:1:1);
   0.00 in 17:3 methylene chloride:methanol
   $R_f$ values by reverse-phase chromatography on Merck-Schuchardt RP-18F 254 slab:
   0.27 in methanol:acetronitrile:25 mM monohydrogen sodium phosphate in water (4:4:2);
   0.35 in methanol:acetronitrile:25 mM dihydrogen potassium phosphate in water+7 mM tetramethylammonium chloride in water (4:4:2);
   0.12 in methanol:10 mM solution of monohydrogen ammonium phosphate in water, adjusted at pH 7.5 with phosphoric acid (8:2);
   0.24 in methanol:acetronitrile:10 mM solution of monohydrogen ammonium phosphate adjusted at pH 7.5 with phosphoric acid (4:4:2); and
   (i) a retention time ($R_t$) of 11.8 minutes by reverse-phase HPLC on Hibar Li-ChroCART Li-Chrosorb RP18 column, forecolumn:Guard Pak RCSS C 18, eluting with methanol:acetronitrile:10 mM aqueous solution of monohydrogen ammonium phosphate (1:1:1), with a flowrate of 0.8 ml/minute at 40° C.

3. Process according to claim 1, in which the fermentation is carried out at temperatures from 20° C. to 35° C.

4. Process according to claim 1, in which the fermentation is carried out at a pH from 5 to 9.

5. Process according to claim 1, in which the AB-021 Antibiotics are subsequently isolated from the fermentation broth by means of filtration and subsequent use of chromatographic techniques.

6. AB-021 Antibiotics obtained by means of the cultivation under aerobic conditions of Streptomyces sp. having all of the identifying characteristics of NCIB 40068, in an aqueous nutrient cultivation medium, containing sources of carbon, nitrogen and inorganic salts, which comprise AB-021a Antibiotic and AB-021b Antibiotic, as defined in claim 1 or 2, and the subsequent separation of said AB-021 Antibiotics.

7. Process for the preparation of AB-021 Antibiotics comprising the cultivation of Streptomyces sp. having all of the identifying characteristics of NCIB 40068, under conditions of aerobic fermentation in an aqueous nutrient medium, containing assimilable sources of carbon, nitrogen and inorganic salts, until said AB-021 antibiotic activity is obtained, and the subsequent recovery of said AB-021 Antibiotics.

8. Process according to claim 7, in which the AB-021 Antibiotics prepared are made up of AB-021a Antibiotic and AB-021b Antibiotic which are subsequently isolated by reverse-phase chromatography on a silicagel column using in the elution a linear gradient of from 30% to 70% of methanol in the mixture constituted by water containing 10 mM/l of monohydrogen ammonium phosphate,
   wherein the AB-021a Antibiotic possesses the following characteristics and properties:
   (a) a good solubility in dimethylsulfoxide and in (1:1 V/V) ethanol/water or (1:1 V/V) methanol/water blends (V/V=volume/volume), poor solubility in water, and rather good solubility in ethanol and methanol;
   (b) an approximate elemental analysis, expressed as % values of:
   carbon: 64.3
   hydrogen: 9.15
   nitrogen: 1.04
   (c) a molecular weight of about 1139;
   (d) maximum absorbance peaks in U.V. light of: 0.193 at 232.8 nm; 2.064 at 318.4 nm; 2.44 at 332.6 nm; 2.113 at 349.6 nm, at a concentration of 0.025 mg/ml of 1:1 (V/V) acetonitrile/water.

(e) maximum absorbance peaks in infrared light at (cm$^{-1}$): 3365; 3015; 2923; 2851; 1700; 1634; 1594; 1541; 1431; 1380; 1329; 1262; 1128; 1095; 1056; 1004; 968; 919; 878; 843; 804; 754;

(f) $^1$H-N.M.R. spectrum, main peaks:

δTMS (ppm): 7.18 (d, 1H); 6.69 (dd, 1H); 6.59 (dd, 1H); 6.52-6.09 (m, 9H); 5.96-5.70 (m, 3H); 5.70-5.31 (m, 8H); 4.27-4.02 (m, 4H); 4.02-3.82 (m, 4H); 3.82-3.58 (m, 4H); 3.30 (t, 1H); 2.82 (t, 2H); 2.73-2.45 (\*) (m, 3H); 2.41-1.98 (m, 13H); 1.91 (s, 3H); 1.79-1.12 (m, 24-25H); 1.00 (d, 3H); 0.95 (d, 3H); 0.89 (d, 3H); 0.85 (d, 3H);

(\*) within this range, also the peak of DMSOd$^6$ is comprised.

(g) $^{13}$-N.M.R. spectrum, main peaks:

δTMS (ppm): 212.1 (s); 169.9 (s); 138.8 (d); 138.5 (d); 137.0 (d); 136.9 (d); 136.7 (d); 136.1 (d); 135.9 (d); 135.9 (d); 134.0 (d); 133.3 (d); 133.0 (d); 132.9 (d); 132.5 (d); 132.4 (d); 132.0 (d); 131.5 (d); 131.0 (d); 131.0 (d); 129.3 (d); 128.9 (d); 128.0 (d); 126.7 (d); 126.4 (d); 125.3 (d); 75.3 (d); 72.3 (d); 71.2 (d); 70.6 (d); 69.7 (d); 68.9 (d); 68.4 (d); 68.0 (d); 67.1 (d); 67.1 (d); 65.7 (d); 64.2 (d); 64.2 (d); 52.1 (d); 41.5 (d); 39.9 (d); 49.2 (t); 46.2 (t); 46.0 (t); 45.2 (t); 45.2 (t); 44.9 (t); 43.9 (t); 41.2 (t); 40.8 (t); 40.7 (t); 39.2 (t); 38.8 (t); 34.1 (t); 32.8 (t); 32.1 (t); 29.3 (t); 24.1 (t); 22.8 (q); 18.4 (q); 13.2 (q); 10.5 (q); 9.1 (q);

(h) R$_f$ values by thin-layer chromatography (TLC) on 60F 254 slab (Merck-Schuchardt):

0.47-0.57 in ethanol:dioxane:aqueous solution of ammonia at 30%:water (8:1:1:1);

0.0 in 17:3 methylene chloride:methanol

R$_f$ values by reverse-phase chromatography on Merck-Schuchardt RP-18F 254 slab:

0.29 in methanol:acetonitrile:25 mM monohydrogen sodium phosphate in water (4:4:2);

0.39 in methanol:acetonitrile:25 mM dihydrogen potassium phosphate + 7 mM tetramethylammonium chloride in water (4:4:2);

0.21 in methanol:10 mM solution of monohydrogen ammonium phosphate adjusted at pH 7.5 with phosphoric acid, in water (8:2);

0.25 in methanol:acetonitrile:10 mM solution of monohydrogen ammonium phosphate adjusted at pH 7.5 with phosphoric acid, in water (4:4:2); and (i) a retention time (R$_t$) of 8 minutes by reverse-phase HPLC on Hibar Li-ChroCART Li-Chrosorb RP-18 column, forecolumn:Guard Pak RCSS C 18, eluting with methanol:acetonitrile:10 mM aqueous solution of monohydrogen ammonium phosphate (1:1:1), with a flowrate of 0.8 mL/minute at 40° C.; and the AB-021 Antibiotic possesses the following characteristics and properties:

(a) maximum absorbance peaks in U.V. light of: 0.90 at 369.0 nm; 2.01 at 350 nm; 2.21 at 332.6 nm; 1.49 at 318.0 nm at a concentration of 0.02 mg/ml in 1:1 (V/V) acetonitrile/water;

(b) maximum absorbance peaks in infrared light at (cm$^{-1}$): 3902, 3853, 3747, 3375, 3013, 2921, 2853, 2757, 1895, 1699, 1669, 1645, 1576, 1540, 1430, 1378, 1324, 1261, 1160, 1094, 1059, 1004, 969, 919, 878, 843, 803, 779, 697;

(c) molecular weight of about 1165;

(d) $^1$H-N.M.R. spectrum, main peaks:

δTMS (ppm): 7.21 (d, 1H); 6.75 (dd, 1H); 6.63 (dd, 1H); 6.57-6.07 (m, 11H); 5.93-5.70 (m, 3H); 5.70-5.33 (m, 8H); 4.25-4.20 (m, 4H); 4.02-3.83 (m, 4H); 3.83-3.59 (m, 4H); 3.29 (t, 1H); 2.82 (t, 2H); 2.72-2.44 (\*) (m, 6-7H); 2.41-2.00 (m, 14H); 1.92 (s, 3H); 1.80-1.14 (m, 21H); 1.00 (d, 3H); 0.95 (d, 3H); 0.84 (d, 3H);

(\*) within this range also the peak of DMSOd$^6$ is comprised;

(e) $^{13}$C-N.M.R. spectrum, main peaks:

δTMS (ppm): 212.0 (s); 169.2 (s); 139.1 (d); 138.1 (d); 137.1 (d); 136.7 (d); 136.2 (d); 135.8 (d); 135.8 (d); 135.1 (d); 133.8 (d); 133.1 (d); 132.8 (d); 132.8 (d); 132.6 (d); 132.3 (d); 132.2 (d); 132.1 (d); 131.8 (d); 131.2 (d); 130.9 (d); 130.8 (d); 129.2 (d); 128.7 (d); 127.9 (d); 126.4 (d); 126.2 (d); 125.2 (d); 75.4 (d); 72.6 (d); 71.0 (d); 70.6 (d); 69.6 (d); 68.9 (d); 68.4 (d); 68.0 (d); 67.3 (d); 67.2 (d); 65.6 (d); 64.4 (d); 64.4 (d); 51.9 (d); 41.3 (d); 39.6 (d); 49.2 (t); 45.8 (t); 45.7 (t); 45.0 (t); 44.9 (t); 44.7 (t); 43.6 (t); 41.1 (t); 40.7 (t); 40.5 (t); 39.0 (t); 38.7 (t); 33.9 (t); 32.5 (t); 31.9 (t); 29.0 (t); 23.9 (t); 18.1 (q); 12.8 (q); 8.7 (q);

(f) R$_f$ values by thin-layer chromatography (TLC) on 60F 254 slab (Merck-Schuchardt):

0.54 in ethanol:dioxane:aqueous solution of ammonia at 30%:water (8:1:1:1);

0.00 in 17:3 methylene chloride:methanol

R$_f$ values by reverse-phase chromatography on Merck-Schuchardt RP-18F 254 slab:

0.27 in methanol:acetonitrile:25 mM monohydrogen sodium phosphate in water (4:4:2);

0.35 in methanol:acetonitrile:25 mM dihydrogen potassium phosphate in water + 7 mM tetramethylammonium chloride in water (4:4:2);

0.12 in methanol:10 mM solution of monohydrogen ammonium phosphate in water, adjusted at pH 7.5 with phosphoric acid (8:2);

0.24 in methanol:acetonitrile:10 mM solution of monohydrogen ammonium phosphate adjusted at pH 7.5 with phosphoric acid (4:4:2); and (i) a retention time (R$_t$) of 11.8 minutes by reverse-phase HPLC on Hibar Li-ChroCART Li-Chrosorb RP18 column, forecolumn:Guard Pak RCSS C 18, eluting with methanol:acetonitrile:10 mM aqueous solution of monohydrogen ammonium phosphate (1:1:1), with a flowrate of 0.8 ml/minute at 40° C.

9. A method of destroying fungus and/or bacteria comprising applying thereto a fungicidally and/or bactericidally effective amount of a compound selected from the group consisting of AB-021 Antibiotics, AB-021a Antibiotic and AB-021b Antibiotic, as defined in claim 1 or 2.

10. Fungicide and/or bactericide compositions containing as their active ingredient a fungicidally and/or bactericidally effective amount of a compound selected from the group consisting of AB-021 Antibiotics, AB-021a Antibiotic and AB-021b Antibiotic, as defined in claim 1 or 2, together with inert solid or liquid carriers.

11. Process according to claim 7, in which the recovery is followed by a separation of the main components, designated as AB-021a Antibiotic and AB-021b Antibiotic, wherein AB-021a Antibiotic has the following characteristics and properties:

(a) a good solubility in dimethylsulfoxide and in (1:1 V/V) ethanol/water or (1:1 V/V) methanol/water blends (V/V=volume/volume), poor solubility in water, and rather good solubility in ethanol and methanol;

(b) an approximate elemental analysis, expressed as % values of:
carbon: 64.3
hydrogen: 9.15
nitrogen: 1.04
(c) a molecular weight of about 1139;
(d) maximum absorbance peaks in U.V. light of: 0.193 at 232.8 nm; 2.064 at 318.4 nm; 2.44 at 332.6 nm; 2.113 at 349.6 nm, at a concentration of 0.025 mg/ml of 1:1 (V/V) acetonitrile/water.
(e) maximum absorbance peaks in infrared light at (cm$^{-1}$): 3365; 3015; 2923; 2851; 1700; 1634; 1594; 1541; 1431; 1380; 1329; 1262; 1128; 1095; 1056; 1004; 968; 919; 878; 843; 804; 754;
(f) $^1$H-N.M.R. spectrum, main peaks:
δTMS (ppm): 7.18 (d, 1H); 6.69 (dd, 1H); 6.59 (dd, 1H); 6.52-6.09 (m, 9H); 5.96-5.70 (m, 3H); 5.70-5.31 (m, 8H); 4.27-4.02 (m, 4H); 4.02-3.82 (m, 4H); 3.82-3.58 (m, 4H); 3.30 (t, 1H); 2.82 (t, 2H); 2.73-2.45 (*) (m, 3H); 2.41-1.98 (m, 13H); 1.91 (s, 3H); 1.79-1.12 (m, 24-25H); 1.00 (d, 3H); 0.95 (d, 3H); 0.89 (d, 3H); 0.85 (d, 3H);
(*) within this range, also the peak of DMSOd$^6$ is comprised;
(g) $^{13}$C-N.M.R. spectrum, main peaks:
δTMS (ppm): 212.1 (s); 169.9 (s); 138.8 (d); 138.5 (d); 137.0 (d); 136.9 (d); 136.7 (d); 136.1 (d); 135.9 (d); 135.9 (d); 134.0 (d); 133.3 (d); 133.0 (d); 132.9 (d); 132.5 (d); 132.4 (d); 132.0 (d); 131.5 (d); 131.0 (d); 131.0 (d); 129.3 (d); 128.9 (d); 128.0 (d); 126.7 (d); 126.4 (d); 125.3 (d); 75.3 (d); 72.3 (d); 71.2 (d); 70.6 (d); 69.7 (d); 68.9 (d); 68.4 (d); 68.0 (d); 67.1 (d); 67.1 (d); 65.7 (d); 64.2 (d); 64.2 (d); 52.1 (d); 41.5 (d); 39.9 (d); 49.2 (t); 46.2 (t); 46.0 (t); 45.2 (t); 45.2 (t); 44.9 (t); 43.9 (t); 41.2 (t); 40.8 (t); 40.7 (t); 39.2 (t); 38.8 (t); 34.1 (t); 32.8 (t); 32.1 (t); 29.3 (t); 24.1 (t); 22.8 (q); 18.4 (q); 13.2 (q); 10.5 (q); 9.1 (q);
(h) R$_f$ values by thin-layer chromatography (TLC) on 60F 254 slab (Merck-Schuchardt):
0.47-0.57 in ethanol: dioxane: aqueous solution of ammonia at 30%: water (8:1:1:1);
0.0 in 17:3 methylene chloride: methanol
R$_f$ values by reverse-phase chromatography on Merck-Schuchardt RP-18F 254 slab:
0.29 in methanol: acetonitrile: 25 mM monohydrogen sodium phosphate in water (4:4:2);
0.39 in methanol: acetonitrile: 25 mM dihydrogen potassium phosphate+7 mM tetramethylammonium chloride in water (4:4:2);
0.21 in methanol: 10 mM solution of monohydrogen ammonium phosphate adjusted at pH 7.5 with phosphoric acid, in water (8:2);
0.25 in methanol: acetonitrile: 10 mM solution of monohydrogen ammonium phosphate adjusted at pH 7.5 with phosphoric acid, in water (4:4:2); and
(i) a retention time (R$_t$) of 8 minutes by reverse-phase HPLC on Hibar Li-ChroCART Li-Chrosorb RP-18 column, forecolumn: Guard Pak RCSS C 18, eluting with methanol: acetonitrile: 10 mM aqueous solution of monohydrogen ammonium phosphate (1:1:1), with a flowrate of 0.8 mL/minute at 40° C.; and
AB-021b Antibiotic has the following characteristics and properties:

(a) maximum absorbance peaks in U.V. light of: 0.90 at 369.0 nm; 2.01 at 350 nm; 2.21 at 332.6 nm; 1.49 at 318.0 nm at a concentration of 0.02 mg/ml in 1:1 (V/V) acetronitrile/water;
(b) maximum absorbance peaks in infrared light at (cm$^{-1}$): 3902, 3853, 3747, 3375, 3013, 2921, 2853, 2757, 1895, 1699, 1669, 1645, 1576, 1540, 1430, 1378, 1324, 1261, 1160, 1094, 1059, 1004, 969, 919, 878, 843, 803, 779, 697;
(c) molecular weight of about 1165;
(d) $^1$H-N.M.R. spectrum, main peaks:
δTMS (ppm): 7.21 (d, 1H); 6.75 (dd, 1H); 6.63 (dd, 1H); 6.57-6.07 (m, 11H); 5.93-5.70 (m, 3H); 5.70-5.33 (m, 8H); 4.25-4.20 (m, 4H); 4.02-3.83 (m, 4H); 3.83-3.59 (m, 4H); 3.29 (t, 1H); 2.82 (t, 2H); 2.72-2.44 (*) (m, 6-7H); 2.41-2.00 (m, 14H); 1.92 (s, 3H); 1.80-1.14 (m, 21H); 1.00 (d, 3H); 0.95 (d, 3H); 0.84 (d, 3H);
(*) within this range also the peak of DMSOd$^6$ is comprised;
(e) $^{13}$C-N.M.R. spectrum, main peaks:
δTMS (ppm): 212.0 (s); 169.2 (s); 139.1 (d); 138.1 (d); 137.1 (d); 136.7 (d); 136.2 (d); 135.8 (d); 135.8 (d); 135.1 (d); 133.8 (d); 133.1 (d); 132.8 (d); 132.8 (d); 132.6 (d); 132.3 (d); 132.2 (d); 132.1 (d); 131.8 (d); 131.2 (d); 130.9 (d); 130.8 (d); 129.2 (d); 128.7 (d); 127.9 (d); 126.4 (d); 126.2 (d); 125.2 (d); 75.4 (d); 72.6 (d); 71.0 (d); 70.6 (d); 69.6 (d); 68.9 (d); 68.4 (d); 68.0 (d); 67.3 (d); 67.2 (d); 65.6 (d); 64.4 (d); 64.4 (d); 51.9 (d); 41.3 (d); 39.6 (d); 49.2 (t); 45.8 (t); 45.7 (t); 45.0 (t); 44.9 (t); 44.7 (t); 43.6 (t); 41.1 (t); 40.7 (t); 40.5 (t); 39.0 (t); 38.7 (t); 33.9 (t); 32.5 (t); 31.9 (t); 29.0 (t); 23.9 (t); 18.1 (q); 12.8 (q); 8.7 (q);
(f) R$_f$ values by thin-layer chromatography (TLC) on 60F 254 slab (Merck-Schuchardt):
0.54 in ethanol: dioxane: aqueous solution of ammonia at 30%: water (8:1:1:1);
0.00 in 17:3 methylene chloride: methanol
R$_f$ values by reverse-phase chromatography on Merck-Schuchardt RP-18F 254 slab:
0.27 in methanol: acetonitrile: 25 mM monohydrogen sodium phosphate in water (4:4:2);
0.35 in methanol: acetonitrile: 25 mM dihydrogen potassium phosphate in water+7 mM tetramethylammonium chloride in water (4:4:2);
0.12 in methanol: 10 mM solution of monohydrogen ammonium phosphate in water, adjusted at pH 7.5 with phosphoric acid (8:2);
0.24 in methanol: acetonitrile: 10 mM solution of monohydrogen ammonium phosphate adjusted at pH 7.5 with phosphoric acid (4:4:2); and
(i) a retention time (R$_t$) of 11.8 minutes by reverse-phase HPLC on Hibar Li-ChroCART Li-Chrosorb RP18 column, forecolumn: Guard Pak RCSS C 18, eluting with methanol: acetonitrile: 10 mM aqueous solution of monohydrogen ammonium phosphate (1:1:1), with a flowrate of 0.8 ml/minute at 40° C.

12. The non-naturally occurring biologically pure culture of Streptomyces sp. having all of the identifying characteristics of the NCIB 40068 microorganism which produces AB-021 Antibiotics in isolatable amounts by means of aerobic fermentation in an aqueous nutrient medium comprising assimilable sources of carbon, nitrogen and inorganic salts.

* * * * *